(12) United States Patent
Foser (10) Patent No.: US 7,325,433 B2
(45) Date of Patent: Feb. 5, 2008

(54) PRESS OVEN INCLUDING AN INTERMEDIATE BODY, AND METHOD FOR USE

(75) Inventor: Hans-Peter Foser, Balzers (LI)

(73) Assignee: Ivoclar Vivadent AG, Schaan (LI)

( * ) Notice: Subject to any disclaimer, the term of this patent is extended or adjusted under 35 U.S.C. 154(b) by 76 days.

(21) Appl. No.: 11/068,421

(22) Filed: Feb. 28, 2005

(65) Prior Publication Data

US 2005/0204796 A1 Sep. 22, 2005

(30) Foreign Application Priority Data

Mar. 19, 2004 (DE) .................... 10 2004 013 668

(51) Int. Cl.
*B21D 37/16* (2006.01)
*A61C 19/00* (2006.01)

(52) U.S. Cl. .................. 72/342.8; 433/34; 264/16

(58) Field of Classification Search ............. 72/20.1, 72/20.2, 38, 342.7, 342.8, 700; 433/34, 40, 433/48, 202.1, 213, 215, 223; 264/16, 19; 249/54

See application file for complete search history.

(56) References Cited

U.S. PATENT DOCUMENTS 5,302,104 A * 4/1994 Ueda ........................ 425/178

5,788,498 A * 8/1998 Wohlwend .................. 433/223
5,948,129 A * 9/1999 Nonami et al. .............. 65/33.1
6,342,458 B1 * 1/2002 Schweiger et al. ............ 501/5
6,484,791 B1 * 11/2002 Vidal ......................... 164/113
6,485,849 B2 * 11/2002 Petticrew .................... 428/697
7,092,780 B2 * 8/2006 Ganley et al. .............. 700/117

FOREIGN PATENT DOCUMENTS

EP 0 231 773 A1 8/1987
JP 11285505 A 10/1999

OTHER PUBLICATIONS

Answers.com, "List of Thermal Conductivities", www.answers.com/topic/list-of-thermal-conductivities. May 11, 2007.*

* cited by examiner

*Primary Examiner*—Ed Tolan
(74) *Attorney, Agent, or Firm*—John C. Thompson; Alan S. Kooman (57) ABSTRACT

A press oven, especially for the pressing of dental material, includes a press stamp via which pressure can be exerted on a blank in a matrix mass of a muffle. An intermediate body is positionable between the press stamp and the blank and the heat conducting capability of the intermediate body (28) is less than that of the blank (26), the press stamp (22) or the matrix mass of the muffle (12).

16 Claims, 3 Drawing Sheets

PRESS OVEN INCLUDING AN INTERMEDIATE BODY, AND METHOD FOR USE

CROSS-REFERENCE TO RELATED APPLICATIONS

This application claims foreign priority benefits under 35 U.S.C. §119 from German patent application Ser. No. 10 2004 013 668.8 filed Mar. 19, 2004.

TECHNICAL FIELD

The present invention relates to a press oven, to an intermediate body for a press oven, and a process for the operation of a press oven.

BACKGROUND OF THE INVENTION

A press oven of this type is disclosed, for example, in EP-A1-231 773. In a press oven of this type, a substantially disk- or flat-cylinder shaped sealing-off piston is pressed downwardly via a press stamp (or piston rod) to apply pressure to a blank that melts as the pressure is exerted thereon. The sealing-off piston is comprised of ceramic and has a diameter that corresponds to the diameter of a feed channel for the blank. Also, the blank is comprised of a ceramic whose consistency and material properties are selected to achieve the desired restoration result.

In connection with such press ovens but, as well, in connection with press ovens that do not have a sealing-off piston—by which, therefore, the press stamp itself applies pressure directly on the blank—the problem exists that the press stamp remains slightly stuck to the ceramic. With respect to the approach disclosed in EP-A1-231 773, a problem additionally exists that the sealing-off piston and the blank intensively interconnect with one another at the deformation temperature of the ceramic and, thus, can only be released following an extensive stress relieving working. One must then practically separate the entire sealing-off piston with a diamond cutter which is time-consuming and wear-intensive. The deployed ceramic masses, in particular with the use of zirconium oxide ceramic, are, in fact, very hard and, in this regard, require a particularly specialized work tool for the separation.

A further problem resides in the fact that the press stamp must exert a considerable pressure to ensure that the ceramic of the blank, which has become soft via the increase in the temperature, penetrates into the branching of the mold cavity in which the restoration pieces should be configured. Upon the beginning of plastification, the pressure to be exerted initially sinks considerably but then, however, increases strongly shortly before the end of the filling of the mold. This leads to a significant increase in the pressure that, in particular, strongly loads the muffle and can lead to the occurrence of spalling locations that detract from the required precision for the production of the dental restoration pieces.

In order to mitigate the effect of this pressure increase, it has already been proposed to deploy a path-/time control that should reduce the pressure at the time of pressure increases and the consequent reduced operation of the press stamp per unit of time. An approach of this type requires, to be sure; a decidedly exact and very rapidly reacting control system for the press operation. Such systems must compensate for, as well, the dead times of the system and are, consequently, expensive.

In order to prevent this, it has heretofore been the practice to operate with a comparatively reduced operational speed. In more recent times, attempts have been undertaken to increase the operational speed in order to improve the cycling time for the preparation and the making available of the dental replacement piece. This requires a still more complex control if a path-/time measurement is to be implemented, to thereby then avoid the feared pressure peaks.

Further in this connection, it has already been proposed to undertake, in lieu of a path-/time measurement, a measurement of the pressure exerted by the press stamp. This approach, however, requires as well a compensation of the dead time in the control system, whereupon such a control system is complex and is, as well, particularly difficult to calibrate.

In this connection, the operational speed of the press stamp is, typically, at a minimum lowered toward the end of the estimated end of the press process. In view of the fact that the positional height of the blank in the muffle differs from one operation to another, the operation is oftentimes operated at reduced speed during practically the entire course of the pressing or, even, for the entirety of the course of the pressing.

The muffle with the blank already disposed therein is typically brought to a preheat temperature in a so-called preheat press oven. Following the placement of the muffle in the press oven, the relatively cold press stamp is traveled downwardly and the press stamp contacts, either via the ceramic sealing-off piston that, in reality, melts together with the ceramic blank or itself directly, the blank so that stresses occur at the same time, and as well, the heat expansion coefficient of the press stamp is regularly clearly greater than the heat expansion coefficient of ceramic.

OBJECTS AND SUMMARY OF THE INVENTION

The present invention offers a solution to the challenge of providing a press oven, an intermediate body, and, as well, a process for the operation of a press oven, which collectively permit a rapid and stress-minimized press cycle with minimum capital costs whereby, however, the operational speed of the press stamp of the press oven is not too greatly limited.

The inventive press oven is characterized by the targeted use of a material for the intermediate body that has a heat conducting capability less than that of the material that encircles it. In this connection, there occurs a clear reduction of the abrupt heat transition between the pre-heated blank and the cold press stamp. Surprisingly, by the use of these measures, stress cracks in the blank due to the sudden temperature reduction are avoided. While the heretofore deployed blanks exhibited, on the sides thereof turned toward the press stamp, stress cracks as a result of the intensive contacts with the press stamp, with such stress cracks having foreclosed the possibility to use these portions of the press stamp, that is, the upper portion of the blank, for the press stamp process, the present invention, conversely, ensures a uniform material quality over the entire blank, even if a rapid process execution is performed during which there is insufficient time to pre-heat the cold press stamp.

In accordance with the present invention, it is particularly favorable, as well, if the material of the intermediate body is chosen so as to have a reduced hardness relative to that of ceramic. The material need not be extended over the entire height of the intermediate body; for the desired buffer effect, an extension of the material over a portion of the height such as, for example, half the height, is sufficient. Via this surprisingly simple measure, the pressure peaks that are introduced via the press stamp can be drastically reduced. In accordance with the present invention, it is particularly advantageous that, as well, the time lags (dead time) introduced via the press stamp operation itself and its mass are compensated for, in that the decidedly small intermediate body buffers, as well, the inertia of the press stamp during rapid movement of the press stamp.

The inventive intermediate body operates, as well, as a separation aid, since, due to the formation of the intermediate body from ceramic as well as from metal, the attachment of the intermediate body to the muffle, which can lead to damage of the muffle, is precluded and, upon cooling off and release of the press stamp, the tendency towards stress cracks is reduced. In this connection, the good heat conducting capabilities of the material of the intermediate body are exploited; also, in this respect, it is basically sufficient if at least one significant portion of the intermediate body is comprised of a material with the reduced hardness.

It is advantageous if the reduced hardness leads to the material of the intermediate body, in the area of interest, being elastically or, as the occasion arises, plastically, deformed during the operation of the pressure increase. The stress peaks during the course of the pressure application are reduced via the deformation so that damage to the muffle does not occur. It is especially favorable in this connection if the material is somewhat compressible. The setting of the modulus of elasticity is preferably effected such that practically no significant deformation occurs during the press operation itself while the deformation sets in towards the end of the press process, that is, upon the increase of pressure, in order to reduce the pressure peaks.

It is also alternatively possible to select the shape stability of a non-compressible material for the intermediate body such that, during the actual press process, still no deformation occurs. In connection with this alternative embodiment, hollow volumes are provided laterally or in the intermediate body that are filled with material via the deformation. An example of such an approach is the configuration of an intermediate body that is, for example, four- or six-sided, and disposed in an annular feed channel for the press stamp. The hollow volumes between the feed channel and the intermediate body are filled via the deformation at the end of the press process without the need to configure the intermediate body with a compressible material.

Materials that can be selected for the intermediate body include asbestos, a sand material, a combustion wad, a gel, or a paste. In connection with at least partially viscous materials, it is to be understood that a sealing off is achieved in the required manner; to this extent, it is advantageous if a type of hull or shell is available into which a gel, a paste or, for example, a powder-shaped or fiber-shaped medium, can be disposed.

The hardness of the material that comprises a substantial portion of the intermediate body should be clearly less than 300 MPa. This can, for example, be ensured via monitoring of the bending resistance. The bending resistance of zirconium oxide ceramic can lie, for example, between 80 and 200 N/mm². The softer material can, in this connection, comprise a bending resistance of, for example, from 10 to 50 N/mm².

It is also advantageous if the heat expansion coefficient of the intermediate body is decidedly low, in particular, clearly less than the heat expansion coefficient of the feed channel or, respectively, the muffle that forms the feed channel. In this manner, it is ensured that the pressure from the inside is exerted on the turns of the muffle upon heating up, which may otherwise increase the friction.

The intermediate body can, as well, be secured either to the press stamp or the blank via a corresponding adhesive coating so that the intermediate body, upon release of the press stamp, remains secured thereto and a clean separation to the other surfaces can then be achieved.

In an advantageous embodiment, it is provided that the heat conducting capability of the intermediate body is less than that of the blank and/or that of the press stamp and/or that of the matrix or embedding mass of the muffle.

In an advantageous embodiment, it is provided that the heat expansion coefficient of the intermediate body is less than 1 W/m*K, especially, less than 0.5 W/m*K and, especially, less than 0.25 W/m*K. Stress cracks in the blank are avoided with the use of such reduced values'.

In an advantageous embodiment, it is provided that the intermediate body is at least partially comprised of a material with a hardness and/or resistance less than that of ceramic and that the blank is, especially, comprised of ceramic or a metal alloy.

In an advantageous embodiment, it is provided that the intermediate body is comprised of at least one coating of a material with a heat conducting capability less than that of the surrounding material and, especially, exhibits as well a reduced hardness. For example, the intermediate body can be assembled together out of at least two materials with differing hardness and, especially, can comprise an outer closed hull whose material differs from at least one further material of the intermediate body.

The configuration of at least a substantial portion of the intermediate body with the desired material properties is sufficient.

In an advantageous embodiment, it is provided that the hull comprises a combustible material combustible upon reaching the deformation temperature of the blank or a temperature resistant material. In connection with combustible material, the intermediate body can, insofar as concerns its hull, be volatized via setting of such volatization relative to the operational temperature. The hull can serve to maintain the shape stability of the intermediate body.

In an advantageous embodiment, it is provided that the blank is comprised of a ceramic mix that, at least, comprises aluminum oxide and/or magnesium oxide and has a heat conducting capability between 6 W/m*K and 30 W/m*K, or a zirconium oxide ceramic with a heat conducting capability between 1.5 and 3 W/m*K, and that the press stamp is comprised of metal and has a heat conducting capability between 80 to 250 W/m*K. Via these values, it is ensured that the intermediate body has a clearly lower heat conducting capability.

In an advantageous embodiment, it is provided that the intermediate body has, on the side thereof facing the press stamp, a smooth and attachment-resistant surface, especially, a slightly curved surface, with a somewhat reduced diameter than that of the press stamp.

In an advantageous embodiment, it is provided that the intermediate body is connected with the blank or with the press stamp and is, especially on its rear side, coated with an adhesive material and adheres to the press stamp or the blank upon the exertion of pressure thereon.

In a further advantageous embodiment, it is provided that the intermediate body is connected in a form fitting or friction fitting manner with the blank or the press stamp and, as the occasion arises, comprises a round outer contour that corresponds substantially to that of the inner contour of the feed channel.

In a further advantageous embodiment, it is provided that the outer shape of the intermediate body is similar to the outer shape of the press and/or the blank and, especially, has a round or many-sided cross section.

In an additional advantageous embodiment, it is provided that the intermediate body is configured as cylindrically-shaped or disk-shaped and its outer dimensions are correspondingly configured with respect to the inner dimensions of a feed channel that feeds the blank into the muffle and that the intermediate body is disposed in the feed channel such that there is no play thereof.

In an additional advantageous embodiment, it is provided that the lateral outer dimensions of the intermediate body are similar to the lateral outer dimensions of the press stamp and/or the blank and, especially, that such dimensions are at reduced values, preferably approximately 0.5 to 10% of the diameter, that are less than those of the press stamp and/or the blank.

The disposition of the intermediate body with the absence of any play ensures that no increase in the coefficient of friction of the blank occurs due to the setting in of the intermediate body.

In an advantageous embodiment, it is provided that the height of the intermediate body, at most, corresponds to the height of the blank and that the intermediate body exhibits a heat expansion coefficient that substantially corresponds to the heat expansion coefficients of the feed channel of the muffle and that the intermediate body comprises a melting temperature of more than 900° C., especially, more than 1200° C., or comprises a lower heat expansion coefficient than that of the muffle surrounding the feed channel.

Via the reduced heat expansion coefficients, it is ensured that the intermediate body does not press on the wall of the feed channel upon the heating up of the feed channel.

In an advantageous embodiment, it is provided that the press oven comprises a blank advancing device operable to dispose the intermediate body under the press stamp. The blank advancing device can comprise a pusher that is arranged substantially at the height of the top side of the muffle and which is operable to dispose a new intermediate body in the feed channel. The blank advancing device can comprise a magazine for intermediate bodies that receives a plurality of intermediate bodies of which one can be engaged by the blank advancing device.

Via the blank advancing device, an automatic operation of the inventive press oven is possible.

In an advantageous embodiment, it is provided that the intermediate body is comprised of at least one material with a lower hardness or resistance than ceramic.

In a further advantageous embodiment, it is provided that the combustion press oven can signal, in an optical manner or an audible manner, the need to push in an intermediate body.

Further advantages, details, and features are set forth in the hereinafter following description of several embodiments with reference to the drawings.

DETAILED DESCRIPTION

Figure 1:
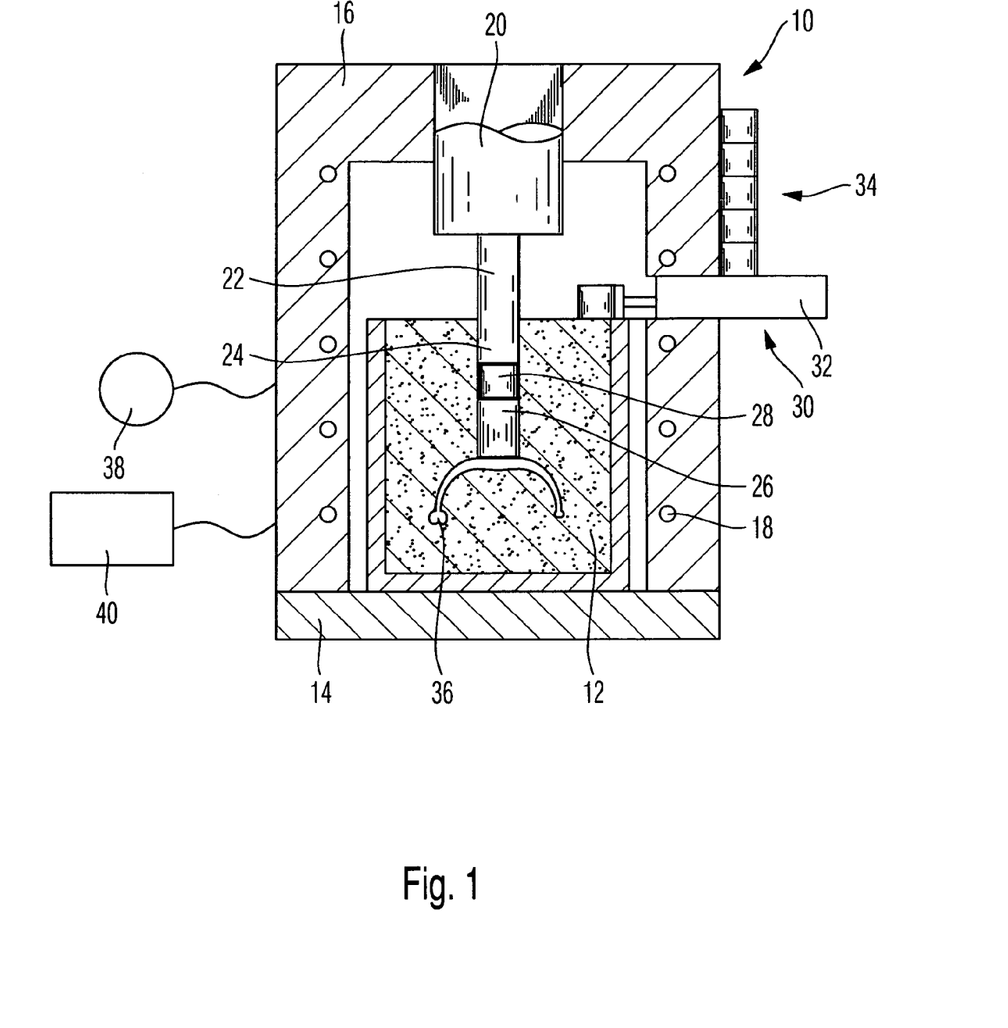
FIG. 1 is a schematic sectional view of a press oven for the deployment in the inventive process.

The press oven 10 shown in FIG. 1 is configured for the receipt of a muffle 12. The press oven comprises a base plate 14 and a press oven hood 16 that receives the heating element 18 of the press oven 10. A press piston 20 is moved in a known manner centrally and from above within the press oven hood 16, the piston transitioning into a press stamp 22 that is in a position to penetrate into a feed channel 24 located in the muffle 12.

In connection with the production of a dental restoration piece, a cylindrically shaped blank 26 of dental material is disposed in the feed channel. In accordance with the present invention, an inventive intermediate body 28 is thereafter disposed in the feed channel 24 before the press stamp 22 is traveled downwardly.

The blank 26 can be comprised either of a ceramic mass such as, for example, aluminum oxide ceramic, a zirconium oxide ceramic, or a mixture of these or, as well, can comprise a metal alloy.

In accordance with this invention a blank or intermediate body 28 is positioned between the press rod 22 and the blank 26. The heat conducting capability of the intermediate body 28 is less than at least one of the blank 26, the press stamp 22 and the matrix mass of the muffle 12. More specifically, the heat conducting capability of the intermediate body 28 is less than 1 W/m*K, more preferably less than 0.5 W/m*K and, most preferably, less than 0.25 W/m*K.

In the embodiment illustrated in FIG. 1, an automatic blank advancing device 30 for feeding intermediate bodies 28 is provided. The blank advancing device 30 comprises a pusher 32 that extends through the press oven hood 16 for pushing out of a magazine 34 the intermediate bodies 28 stored in the magazine. The respective lowermost intermediate body 28 is engaged by the pusher 28 and then advanced to the feed channel 24 via the working of the pusher 32. The intermediate body falls into the feed channel 24 onto the top side of the blank 26, whereby the intermediate body preferably has a diameter less than that of the feed channel 24 and, thus, assumes the proper flat-lying position automatically.

The intermediate body 28 is, in this embodiment, configured in a flat cylinder shape.

In connection with the operation of the inventive press oven, initially, the press piston 20 is maintained in its upper position. The pusher is in its retracted position so that it covers the underside of the magazine 34.

The press oven hood 16 is raised and, initially, the pre-heated muffle 12 is brought into the proper position below the press stamp 22. Following the closure of the press oven hood 16, the pusher 32 is initially operated in order to dispose an intermediate body 28 in the feed channel 24. The intermediate body 28 contacts the blank 26 and is thus subjected to heating up in that the muffle 12 has already been preheated to, for example, a temperature of approximately 900° C.

The still-cold press stamp 22 can then be lowered contemporaneously with the further heating of the muffle 12 via the heating element 18. A predetermined pressure is exerted and, as soon as the blank 26 can be deformed, the press stamp 22 penetrates further into the feed channel 24. The now deformable ceramic mass of the blank 26 distributes itself into the mold 36 to form the dental restoration piece, whereby the mold 36 can, as the occasion arises, also be constructed with small dimension members.

In a preferred embodiment, a vacuum press oven is provided. In connection with such a press oven, the interior volume with the muffle 12 is subjected to a vacuum pressure during the heating up process so that a vacuum is created in the hollow volumes in the muffle 12. The filling of the mold 36 is facilitated by this vacuum, as is conventionally known.

Already upon the engagement of the press stamp 22 on the intermediate body 28 there is a slight deformation of the intermediate body. As soon as the mold 36 is completely filled with the material of the blank 26, the counter pressure that is exerted on the muffle 12 onto the press stamp 22 rises strongly and, in fact, rises suddenly. This sudden pressure increase is minimized via the inventive intermediate body 28. The intermediate body deforms somewhat further so that no pressure peaks occur while, instead, an exclusively steep pressure increase curve occurs. The deformation itself can follow in the desired suitable manner, whereby, in connection with the hereinafter described various embodiments of the intermediate body, attention is drawn to the deformation process.

As soon as the condition of maximum pressure is reached, the present pressure on the press piston 20 is maintained solely for the purpose that, in a known manner, a material securement of the ceramic used for the blank 26 occurs and the occurrence of micro hollow volumes is foreclosed. The grain boundaries in the deployed ceramic are melted via the combination of pressure and temperature and the desired structure sets in, as is conventionally known. Also, in this condition, the inventive intermediate body 28 maintains the pressure exerted thereupon and further transmits such pressure to the mass of the ceramic blank.

In a modified embodiment, there follows, in this condition, a volume reduction of the intermediate body 28. This can be achieved, for example, in that additional material for the intermediate body in the form of combustion wad material is provided. The combustion wad is then preferably so configured that it undergoes a volume change first upon reaching a decidedly high temperature and at least partially combusts. In this manner, the pressure can be reduced in a targeted manner whereby it is advantageous that, via the release of the combustion wad, the mechanical connections, as well, are lifted at the same time. To this extent, the combustion wad of the intermediate body operates at the same time as a separation aid.

It is preferred that a surface of the intermediate body 28 that is, either the bottom surface or the upper surface, is so configured that a separation thereat after conclusion of the press process is comparatively easy.

In this connection, for example, the respective surface of the intermediate body can be polished. The upper surface can also be provided with a metallic coating that lies closely to the rear surface of the press stamp 22.

As can be seen in FIG. 1, suitable signal and service devices 38 and 40 are provided for control of the inventive press oven. It is to be understood that, in lieu of the manual operation of the pusher 32, an automatic feed of the inventive intermediate bodies is also possible.

Figure 2:
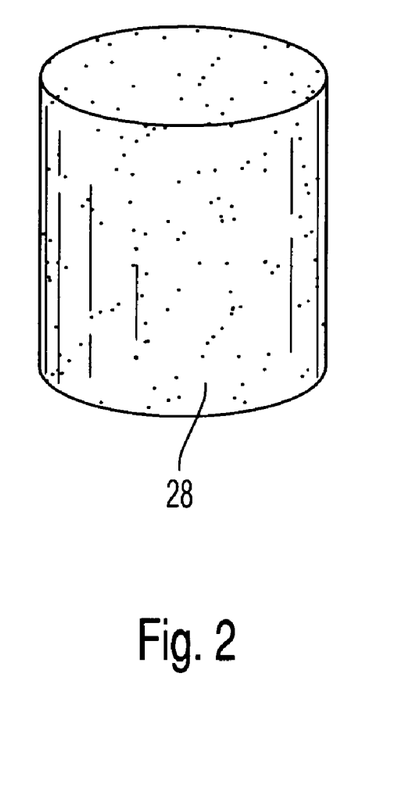
FIG. 2 is a view of an embodiment of the inventive intermediate body.

An intermediate body 28 can be seen in FIG. 2 that is comprised of pressed powder. A powder of this type can have a similar character to that of a ceramic but, in accordance with the invention, should comprise a relatively lower hardness. It is also possible to provide, for example, in the lower half of the intermediate body 28, a particularly soft material and to configure the upper half of, for example, the same zirconium oxide ceramic that is used for the blank 26.

Figure 3:
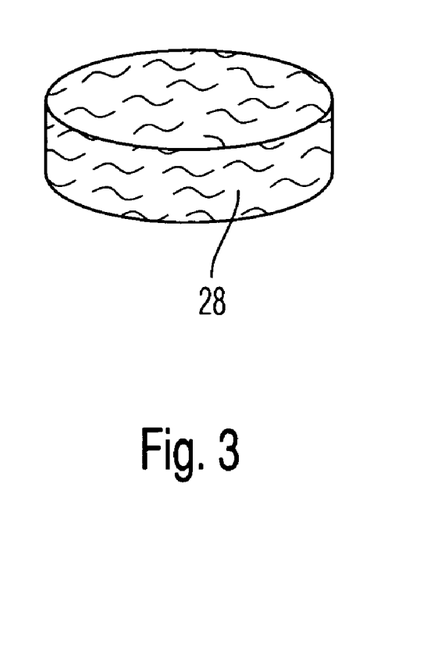
FIG. 3 is a view of a further embodiment of the inventive intermediate body.

The embodiment of the intermediate body shown in FIG. 3 comprises a type of felt formed of pressed fibers that turn to ash already upon reaching the press temperature. The ashes then work as a slightly compromisable intermediate body and make possible an easy separation between the press stamp 22 and the dental restoration piece.

Figure 4:
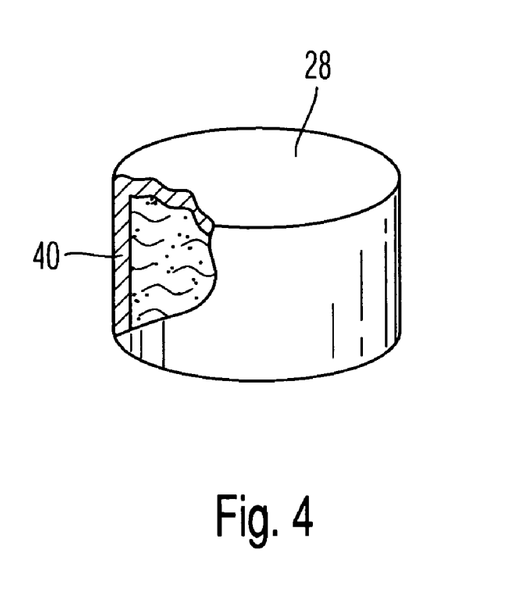
FIG. 4 is a view of yet a further embodiment of the inventive intermediate body.

A modified intermediate body 28 can be seen in FIG. 4. The intermediate body 28 comprises a hull 40 that is enclosed by a mixture of powder and/or fibers and that is deformable. Via the increase in pressure toward the end of the press cycle, the hull can burst or split, whereby the desired deformation is produced. It is to be understood that, in lieu of this, it can also be provided that solely the hull itself is deformable along its extent while, however, the pressures and temperatures that obtain do not operate to destroy the hull.

Figure 5:
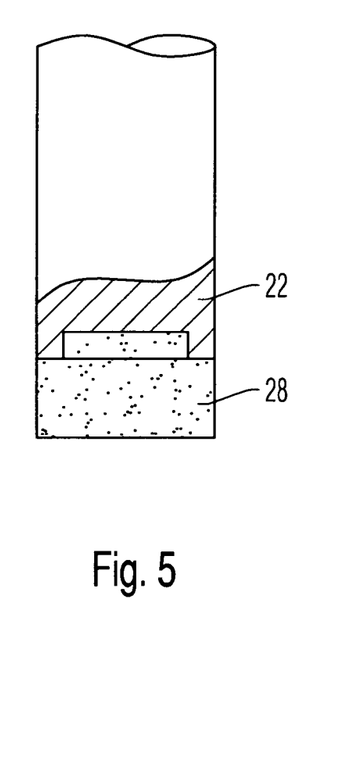
FIG. 5 is a view of another embodiment of the inventive intermediate body.
Figure 6:
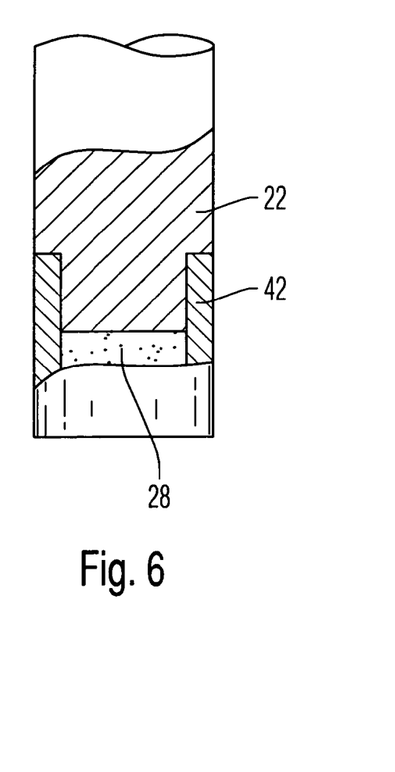
FIG. 6 is a view of a further embodiment of the inventive intermediate body.

The intermediate bodies 28 shown in FIGS. 5 and 6 can be secured to the press stamp 22. In this connection, the typically planar rear surface of the press stamp 22 is modified, as seen in FIG. 5, with a recess and, in FIG. 6, is modified with a tube 42 that holds the material of the intermediate body 28 in a form fitting manner. The intermediate body 28 comprises an outer closed hull whose material is different from at least one further material of the intermediate body 28. The hull (40) is comprised of a temperature resistant material or, alternatively, of a material capable of combusting at the deformation temperature of the blank 26. In an advantageous embodiment, the height of the intermediate body 28, at most, corresponds to the height of the blank 26. The intermediate body exhibits a heat expansion coefficient that substantially corresponds to the heat expansion coefficients of the feed channel 24 of the muffle 12. The intermediate body comprises a melting temperature of more than 900° C., especially, more than 1200° C., or comprises a lower heat expansion coefficient than that of the muffle surrounding the feed channel. The intermediate body 28 has a heat conducting capability less than at least one of the matrix mass of the muffle 12, the material of a press stamp of the press oven 10, and the material of the blank 26. The intermediate body 28 is comprised of at least one material with a hardness or a bending resistance less than that of ceramic. In addition, the heat conducting capability of the intermediate body (28) is less than 1 W/m*K, more preferably less than 0.5 W/m*K, and, most preferably, less than 0.25 W/m*K.

Figure 7:
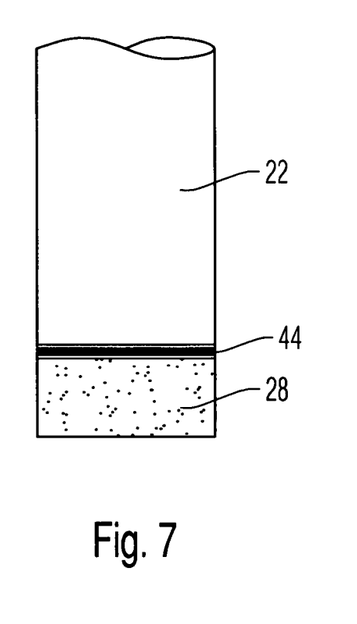
FIG. 7 is a view of a different embodiment of the inventive intermediate body.
Figure 8:
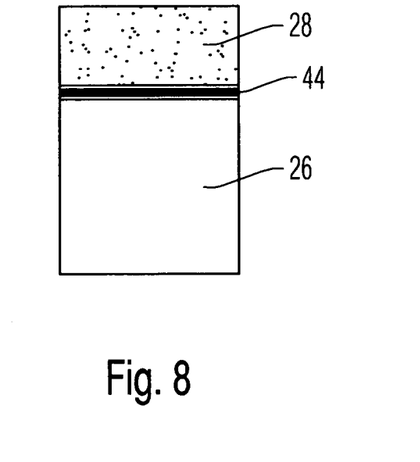
FIG. 8 is a view of a further additional embodiment of the inventive intermediate body.

FIGS. 7 and 8 schematically show the configuration of an adhesive coating 44, whereby the adhesive coating 44 is, in connection with the embodiment shown in FIG. 7, provided between the piston 22 and the intermediate body 28 while the adhesive coating in the embodiment shown in FIG. 8 is provided between the intermediate body 28 and the ceramic blank 26.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A press oven (10), especially for the pressing of dental material (26), comprising:
   a press stamp (22) via which pressure can be exerted on a blank (26) of dental material in a matrix mass of a muffle (12); and
   an intermediate body (28) positionable between the press stamp (22) and the blank (26), the heat conducting capability of the intermediate body (28) being less than or equal to 0.5 W/m*K and being less than at least one of the blank (26), the press stamp (22) and the matrix mass of the muffle (12), wherein the intermediate body (28) comprises at least two materials, one material with a heat conducting capability and/or hardness less than the of at least one further material.

2. A press oven according to claim 1, wherein the beat conducting capability of the intermediate body (28) is less than or equal to 0.25 W/m*K.

3. A press oven according to claim 1, wherein the intermediate body (28) is at least partially comprised of a material having a hardness less than that of ceramic.

4. A press oven according to claim 1, wherein the press oven (10) comprises a blank advancing device (30) that is operable to advance the intermediate body (28) into a position under the press stamp (22).

5. A press oven according to claim 4, wherein the blank advancing device (30) comprises a pusher (32) that is arranged substantially at the height of the top side of the muffle (12) and is operable to advance a fresh intermediate body (28) to a feed channel (24).

6. A press oven according to claim 4, wherein the blank advancing device (30) includes a magazine (34) for intermediate bodies that receives a plurality of intermediate bodies of which individual ones can be engaged by the blank advancing device (30).

7. A press oven (10), especially for the pressing of dental material (26), comprising:
   a press stamp (22) via which pressure can be exerted on a blank (26) of dental material in a matrix mass of a muffle (12); and
   an intermediate body (28) positionable between the press stamp (22) and the blank (26), wherein the intermediate body (28) comprises an outer closed hull whose material is different from at least one further material of the intermediate body (28), and wherein the hull (40) is comprised of a material capable of combusting at the deformation temperature of the blank (26).

8. A press oven according to claim 7, wherein the intermediate body (28) is connected with a selected one of the blank (26) and the press stamp (22).

9. A press oven according to claim 7, wherein the intermediate body (28) is connected in a form-fitting manner with a selected one of the blank (26) and the press stamp (22).

10. A press oven according to claim 7, wherein the intermediate body (28) has an outer contour that cones ponds essentially to an inner contour of a feed channel (24) for the blank in the muffle (12) or to an outer shape of the press stamp (22) and/or the blank (26).

11. A press oven according to claim 7, wherein the intermediate body (28) is cylindrically shaped or disk shaped.

12. An intermediate body for use in a press oven that is operable to press heated dental material in the form of a blank in a muffle, wherein the intermediate body (28) has a heat conducting capability less than or equal to 0.5 W/m*K and at least one of the matrix mass of the muffle (12), the material of a press stamp of the press oven (10), and the material of the blank (26).

13. An intermediate body according to claim 12, wherein the intermediate body (28) is comprised of at least one material with a hardness or a bending resistance less than that of ceramic.

14. A method for operating a press oven in which preheated dental material is subjected to pressing, comprising:
   before a press-/combustion-cycle of the press oven (20), disposing an intermediate body (28) between a press stamp (22) and a blank (26) via, in particular,
   automatically advancing the intermediate body (28) into position, the beat conducting capability of the intermediate body (28) being less than or equal to 0.5 W/m*K and less than at least one of the blank (26), the press stamp (22) and a matrix mass of a muffle (12) located in the press oven.

15. A method according to claim 14, wherein the combustion press oven signals, in an optical maimer or an audible manner, the need to push in an intermediate body (28).

16. An intermediate body for use in a press oven that is operable to press heated dental material in the form of a blank in a muffle, wherein the intermediate body (28) has a heat conducting capability less than at least one of the matrix mass of the muffle (12), the material of a press stamp of the press oven (10), and the material of the blank (26), and further wherein the intermediate body (28) comprises an outer closed hull whose material is different from at least one further material of the intermediate body (28), and wherein the hull (40) is comprised of a material capable of combusting at the deformation temperature of the blank (26).

* * * * *

UNITED STATES PATENT AND TRADEMARK OFFICE
CERTIFICATE OF CORRECTION

PATENT NO. : 7,325,433 B2
APPLICATION NO. : 11/068421
DATED : February 5, 2008
INVENTOR(S) : Hans-Peter Foser Page 1 of 1

It is certified that error appears in the above-identified patent and that said Letters Patent is hereby corrected as shown below:

Claim 2, line 1, change "beat" to --heat--.

Signed and Sealed this

Third Day of June, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,325,433 B2 | Page 1 of 1 |
| APPLICATION NO. | : 11/068421 | |
| DATED | : February 5, 2008 | |
| INVENTOR(S) | : Hans-Peter Foser | |

It is certified that error appears in the above-identified patent and that said Letters Patent is hereby corrected as shown below:

<u>Column 9</u>

Claim 2, line 19, change "beat" to --heat--.

This certificate supersedes the Certificate of Correction issued June 3, 2008.

Signed and Sealed this

First Day of July, 2008

JON W. DUDAS
*Director of the United States Patent and Trademark Office*